(12) United States Patent
Cinelli et al.

(10) Patent No.: US 6,921,574 B2
(45) Date of Patent: Jul. 26, 2005

(54) HYDROGEL ADHESIVES FOR USE ON HAIR OR FIBER-POPULATED SURFACES

(75) Inventors: Fabio Cinelli, Pescara (IT); Peter Coles, Hamilton, OH (US); Stephen Allen Goldman, Città Sant' Angelo (IT); Mario Romano, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 52 days.

(21) Appl. No.: 10/396,645

(22) Filed: Mar. 25, 2003

(65) Prior Publication Data

US 2003/0187115 A1 Oct. 2, 2003

(30) Foreign Application Priority Data

Mar. 29, 2002 (EP) ............................................. 02447052

(51) Int. Cl.⁷ ............................. B32B 15/04; B32B 7/12
(52) U.S. Cl. ...................... 428/350; 428/339; 428/349; 428/355 R; 424/443; 424/449; 604/344
(58) Field of Search ............................. 428/35.2, 35.7, 428/332, 339, 343, 350, 346, 355 R, 349; 424/443, 449; 604/332, 344

(56) References Cited

U.S. PATENT DOCUMENTS

| | | |
|---|---|---|
| 5,728,146 A | 3/1998 | Burkett et al. |
| 5,741,318 A | 4/1998 | Ouellette et al. |
| 2002/0026005 A1 | 2/2002 | Munro |

FOREIGN PATENT DOCUMENTS

| | | |
|---|---|---|
| EP | 1 025 823 A1 | 8/2000 |
| EP | 1 025 866 A1 | 8/2000 |
| EP | 1 026 219 A1 | 8/2000 |
| EP | 1 245 240 A1 | 10/2002 |
| WO | WO 97/36968 | 10/1997 |
| WO | WO 97/49361 | 12/1997 |
| WO | WO 99/00084 | 1/1999 |
| WO | WO 99/00085 | 1/1999 |
| WO | WO 00/07636 | 2/2000 |

*Primary Examiner*—Michael C. Miggins
(74) *Attorney, Agent, or Firm*—Peter D. Meyer; Julie A. McConihay

(57) ABSTRACT

The present invention relates to the use, for adhesion on hair or fiber-populated surfaces, of hydrogel adhesive characterized by a $G'_{25}$, (1 rad/sec) or below 1000 Pa, resulting in embedding of the hair of fiber and good adhesion properties on the surface.

The invention also encompasses Personal Care Products and Surface Care Articles containing the hydrogel compositions herein.

8 Claims, No Drawings

HYDROGEL ADHESIVES FOR USE ON HAIR OR FIBER-POPULATED SURFACES

FIELD OF THE INVENTION

The present invention relates to hydrogel adhesives for attachment to hair or fibers populated surfaces in particular skin, and to Personal Care or Surface Care products containing such hydrogels.

BACKGROUND OF THE INVENTION

While the use of hydrogel body adhesives in the of medical field, such as skin electrodes, transdermal drug delivery and wound healing, has been known for several years, hydrogel body adhesives have been disclosed more recently for use in consumer products such as absorbent articles and human waste-management articles; representative of the latter disclosures are EP 1 025 823 and EP 1 025 866, where certain needs specific for such consumer products waste-management products, are addressed, including secure attachment, painless removal and stability of adhesion in presence of excess moisture.

However a particular problem which has not been addressed in said prior art is the ability of the adhesive to adhere directly to a skin surface which has hair present, particularly areas of dense hair growth such as occurs in, e.g., the genital area. Typically the prior art teaches especially in wound care applications, and for incontinence applications such as ostomy articles to remove the hair follicles present on the skin by shaving for example prior to the application of the adhesive. However, such practices whilst moderately acceptable in medical circumstances are not desirable for products which are intended for everyday use for example absorbent articles such as sanitary napkins or incontinence devices such as human waste management devices. The absence of the hair on the skin thereby allows a gasket to be formed with the skin which is necessary in order to ensure the containment of the excreted fluids within the particular device of usage. The prior art does not however address how such gasketing can be achieved without the indignity of removing hair.

Not only does the presence of hair on the skin increase the difficulty to obtain optimum adherence to the skin of the wearer, in addition due to the adhesion which occurs between the hair and the adhesive itself, which typically involves some embedding of the hair within the hydrogel adhesive gel matrix, the removal of the adhesive from the wearer is also extremely painful and is significantly increased versus a skin surface where any hair present has been previously removed.

Thus is it highly desirable to provide a hydrogel adhesive for adhesion to the skin which adheres on skin surfaces which have hair present and which have a reduced pain level on removal of the adhesive. It is further desirable to provide an adhesive which adheres to the skin of a hair populated skin surface but which only has minimal and preferably substantially no adhesion to the hair itself.

It is further desirable to provide an adhesive which can embedded the hair and adhere directly to the skin, thus providing good gasketing, while still allowing painless removal.

It is still another objective of the present invention to provide an adhesive that exhibits an ability to adhere to skin upon reapplication, particularly multiple reapplication for example when the adhesive is misplaced, whilst still allowing painless removal.

It has now been surprisingly found that the above drawbacks will be substantially alleviated by the use of certain hydrogel adhesives with rheology characteristics as defined hereinafter; through said use, attachment to the skin is secure, even if hair is present, the hydrogel is pleasing to the skin upon application, and yet causes no discomfort upon removal and minimal residues.

Finally it has been found that the benefits of the use and of the hydrogels herein can be applied not only to skin populated with hair, but to more generally to surfaces populated with fibers, and thus the present invention also applies to the use of hydrogel with selected characteristics, for surface care articles.

SUMMARY OF THE INVENTION

In a first embodiment herein, the present invention is directed to the use, for adhesion on hair or fiber-populated surfaces, of hydrogel adhesives comprising 10–60 wt % of a cross-linked hydrophilic polymer, 5–80 wt % of a water-soluble nonionic humectant and 10–85 wt % water, said adhesive having a viscous modules at a temperature of 25° C., $G'_{25}$, selected such that $G'_{25}$ (1 rad/sec) is less than 1000 Pa, preferably from 100 to 700 Pa.

In a second and third embodiment herein, the present invention provides personal care products capable of adhering to hair-populated skin, and surface-care articles capable of adhering to fiber-populated surface, said personal care products and surface care articles comprising a hydrogel adhesive as defined in the first embodiment.

The hydrogel adhesives herein preferably have the ratio of $G''_{25}$ (1 rad/sec)/$G'_{25}$ (1 rad/sec) is in the range of 0.15 to 0.65 preferably 0.15 to 0.35 and the peel strength force on dry skin is in the range than 0.3 to 3 N/cm preferably 0.3 to 2 N/cm.

DETAILED DESCRIPTION

In a first embodiment herein, the present invention is directed to the use, for adhesion on hair or fiber-populated surfaces, of hydrogel adhesives comprising 10–60 wt % of a cross-linked hydrophilic polymer, 5–80 wt % of a water-soluble nonionic humectant and 10–85wt % water. The polymerization of the monomers preferably takes place in presence of the nonionic humectant and water and cross-linking creates a 3-dimensional matrix for the polymer, also referred to as gel form and hydrogel, as will be described in more detail hereinafter. A critical factor of the hydrogels herein is rheology, is particularly the elastic behavior.

Rheology

The viscous behavior of an adhesive can be interpreted to represent an indication of the ability of the adhesive to quickly attach and securely adhere to a particular surface. The elastic behavior can be interpreted as an indication of the "hardness" behavior of the adhesive. Its value is also important for good initial attachment. Their combination is believed to be an indicator of the required force upon removal. The relation between elastic and viscous modulus is considered to be an indication on which fraction of the removal energy will be dissipated within the adhesive and which fraction is available to trigger the actual removal.

While not being bound by theory, it is believed that for hydrogels applied to skin, the rheological properties at T=37° C. are most relevant to adhesion and removal properties. However, for the hydrogels of this invention, it has been found that the rheology properties are only at most moderately sensitive to temperature in the range of 25–37° C. Thus, for the purpose of this invention, it is convenient to specify the rheological properties at a temperature of 25° C. The adhesive has an elastic modulus (also referred to as storage modulus) at a temperature of 25° C. abbreviated $G'_{25}$, a viscous modulus at a temperature of 25° C. of $G''_{25}$, and the ratio of $G''_{25}/G'_{25}$ at 25° C., referred to as tan $\delta_{25}$.

The elastic modulus (G') of the adhesive is a significant factor which influences the ability of hairs or fibers to be embedded within the hydrogel. Hydrogels with high values of G' are typically too stiff for hairs to be embedded to a significant degree and, for those hairs that do become embedded, too rigid to allow for facile removal without pain. The $G'_{25}$ (1 rad/sec) of the present invention is selected to be less than 1000 Pa, preferably in the range of from 100 Pa to 1000 Pa, more preferably in the range of 100–700 Pa, and even most preferably in the range of 100–500 Pa.

The nature of the hair or fibers also affects the ability of the hair or fiber to penetrate into the hydrogel adhesive. For hair, it has been found that, in particular, the caliper, length, density, and curliness of the hair, which can vary with hair type, impacts the upper value of G' consistent with good penetration of hair into the hydrogel, allowing good gasketing and adhesion of the hydrogel to the underlying skin. It has been determined that the following equation relates the upper value of $G'_{25}$, (1 rad/s) in Pascals (Pa) consistent with good hair penetration to hair characteristics, based on hair from a referenced 1 sqcm area.

$$G'_{25}(1 \text{ rad/sec}) < E/(W*C)$$

wherein:
W=weight of hair per unit area of skin in g/cm$^2$
C=hair curliness factor (ratio of length of stretched to unstretched hair)
E=Numerical Factor for Hair Penetration in units of Pa*g/cm$^2$ We have found that for essentially complete penetration of hair the value for E is 24, preferably 19, even more preferably 9. Thus, for example, if the average value of W for a population type in a relevant 1 sqcm area for adhesion is determined to be 0.02 g/cm$^2$, the average curliness factor for this hair based on microscopy analysis of the removed hairs is 1.2, then for E=24, the value of $G'_{25}$, must be less than 1000 Pa to ensure good embedding of the hair into the hydrogel and thus good gasketing.

The hair or fiber-embedding performance of the adhesive hydrogels herein can be measured by the degree of gasketing provided to the surface to which the hydrogels are applied; and a test method is described hereinafter. The hydrogels herein provide a degree of gasketing significantly higher compared to adhesive hydrogels having a elastic modulus above the present claimed range.

As mentioned above, the viscous modulus of the adhesive is also a significant factor which influence performance, and thus the $G''_{25}$ (1 rad/sec) of the present invention lie in the range of from 50 Pa to 1000 Pa, preferably from 100 Pa to 700 Pa.

Furthermore, the value of tan $\delta_{25}$ (1 rad/sec) directly influences the cohesiveness of the adhesive hydrogels, thus the ability of the hydrogel to disengage from the surface, the hair of the fibers, without leaving residues. The tan $\delta_{25}$ (1 rad/sec) for the hydrogel herein should preferably be less than 0.65, preferably in the range from 0.15 to 0.55, more preferably in the range of 0.15–0.35.

Peel Force

It is a preferred characteristic of the hydrogels herein that their peel force, despite the fact the elastic modulus and tan δ have relatively low values (to ensure respectively good hair or fiber embedding and a high level of cohesiveness), is maintained at an appropriate, value allowing to exhibit excellent adhesion performance on surfaces such as skin. In order to ensure the required skin adhesion initially, and preferably over the entire period of wearer, the adhesive has a peel strength on dry skin of from 0.1 N/cm to 5 N/cm, preferably from 0.3 N/cm to 3 N/cm most preferably 0.3 N/cm to 2 N/cm as determined according to the test method described herein. The peel force of the hydrogel herein, as measured on dry skin, should be in the range of from 0.1 to 5 N/cm, preferably 0.3 to 3 N/cm.

Main Ingredients

According to the present invention the 3-dimensional matrix also referred to herein as a gel, comprises as an essential component a polymer which can be physically or chemically cross-linked. The polymer may be naturally or synthetically derived. The uncrosslinked polymer includes repeating units derived from vinyl alcohols, vinyl ethers and their copolymers, carboxy vinyl monomer, vinyl ester monomers, esters of carboxy vinyl monomers, vinyl amide monomers, hydroxy vinyl monomers, cationic vinyl monomers containing amines or quaternary groups, N-vinyl lactam monomer, polyethylene oxides, polyvinylpyrrolidon (PVP), acrylics such as hydroxyethylmethacrylate, methoxydiethoxyethyl methacrylate, hydroxydiethoxyethyl methacrylate, acrylic acid and acrylates and sulphonated polymers such as acrylamide sulphonated polymers, sulphopropylacrylates and mixtures thereof. Alternatively, the uncrosslinked polymer may be a homopolymer or copolymer of a polyvinyl ether, or a copolymer derived from half ester of maleic ester. Similarly any other compatible polymer monomer units may be used as copolymers such as for example polyvinyl alcohol and polyacrylic acid or ethylene and vinyl acetate.

As another alternative, the polymers may be block copolymer thermoplastic elastomers such as ABA block copolymers such as styrene-olefin-styrene block copolymers or ethylene-propylene block copolymers. More preferably such polymers include hydrogenated grade Styrol/Ethylene-Butylene/Styrol (SEBS), Styrene/Isoprene/Styrene (SIS), and Styrol/Ethylene-Propylene/Styrol (SEPS).

Particularly preferred polymers are acrylics, sulphonated polymers such as acrylamide sulphonated polymers, vinyl alcohols, vinyl pyrrolidine, polyethylene oxide and mixtures thereof.

The polymers herein can also be made of monomers which are selected from strong-acid monomers, weak-acid monomers, nonionic, cationic or zwitterionic monomers.

Strong-acid monomers is defined in relation to their pKa, which must be below 3. The pKa is measured by titration of the acid with strong base in aqueous solution according to methods well known in the art. The said strong-acid monomers are preferably selected from the group of olefically unsaturated aliphatic or aromatic sulfonic acids such as 2-acrylamido-2-methylpropanesulfonic acid, 3-sulphopropyl (meth)acrylate, 2-sulfoethyl (meth)acrylate, vinylsulfonic acid, styrene sulfonic acid, allyl sulfonic acid, vinyl toluene sulfonic acid, methacrylic sulfonic acid and the like. Particularly referred strong-acid monomers are 2-acrylamido-2-methylpropanesulfonic acid, 3-sulfopropyl (meth)acrylate, 2-sulfoethyl (meth)acrylate.

Weak acid monomers are defined in relation to their pKa, which must be above 3. The said monomers are preferably selected from the group of olefinically unsaturated carboxylic acids and carboxylic acid anhydrides such as acrylic acid, methacyclic acid, maleic acid, itaconic acid, crotonic acid, ethacrylic acid, citroconic acid, fumaric acid, δ-sterylacrylic acid and the like. Particularly preferred weak-acid monomers are acrylic acid and methacrylic acid.

Examples of nonionic monomers include N,N-dimethylacrylamide, acrylamide, N-isopropyl acrylamide, hydroxyethyl (meth)acrylate, hydroxypropyl (meth)acrylate, alkyl (meth)acrylates, N-vinyl pyrrolidone and the like. Examples of cationic monomers include N,N-dimethylaminoethyl (meth)acrylate, N,N-dimethylaminoethyl (meth)acrylamide and the respective quaternary salts and the like.

Humectant

The 3-dimensional adhesive matrix also comprises a humectant or mixture of humectants (also referred herein as a plastisizer), which is preferably a liquid at room temperature. The humectant is selected such that the monomer and polymer may be solubilized or dispersed within. For embodiments wherein irradiation cross linking is to be carried out, the humectant is desiderably irradiation cross linking compatible such that is does not significantly inhibit the irradiation cross linking process of the polymer. The components of the humectant mixture are preferably hydrophilic and miscible with water.

Suitable humectants include alcohols, polyhydric alcohols such as glycerol and sorbitol, and glycols and ether glycol such as mono- or diethers of polyalkylene glycol, mono- or diester polyalkylene glycols, polyethylene glycols (typically up to a molecular weight of about 600), glycolates, glycerol, sorbitan esters, esters of citric and tartaric acid, imidazoline derived amphoteric surfactants, lactams, amides, polyamides, quaternary ammonium compounds, esters such as phthalates, adipates, stearates, palmitates, sebacates, or myristates, glycerol esters, including mono/di/tri-glycerides, and combinations thereof. Particularly preferred are polyhydric alcohols, polyethylene glycol (with a molecular weight up to about 600), glycerol, sorbitol and mixtures thereof. Glycerol is especially preferred. The humectant comprises 5–80 wt % of the hydrogel.

An important function of the humectant is to reduce the water activity of the hydrogel to 0.35–0.95, preferably 0.4–0.85, most preferably from 0.45–0.75. Water activity is determined by measuring the equilibrium relative humidity above the hydrogel according to the method described hereinafter in the test methods section.

Suitable humectants include alcohols, polyhydric alcohols such as glycerol and sorbitol, and glycols and ether glycol such as mono- or diethers of polyalkylene glycol, mono- or diester polyalkylene glycols, polyethylene glycols (typically up to a molecular weight of about 600), glycolates, glycerol, sorbitan esters, esters of citric and tartaric acid, imidazoline derived amphoteric surfactants, lactams, amides, polyamides, quaternary ammonium compounds, esters such as phthalates, adipates, stearates, palmitates, sebacates, or myristates, glycerol esters, including mono/di/tri-glycerides, and combinations thereof. Particularly preferred are polyhydric alcohols, polyethylene glycol (with a molecular weight up to about 600), glycerol, sorbitol and mixtures thereof. Glycerol is especially preferred. The humectant comprises 5–80 wt % of the hydrogel.

An important function of the humectant is to reduce the water activity of the hydrogel to 0.35–0.95, preferably 0.4–0.85, most preferably from 0.45–0.75. Water activity is determined by measuring the equilibrium relative humidity above the hydrogel according to the method described hereinafter in the test methods section.

Polymerization Conditions

According to the present invention the polymer component of the adhesive can be physically, chemically or ionically cross linked in order to form the 3 dimensional matrix. Physical cross linking refers to polymers having cross links which are not chemical covalent bonds but are of a physical nature such that for example there are three areas in the 3 dimensional matrix having high crystallinity or areas having a high glass transition temperature or areas having hydrophobic interactions. Chemical cross linking refers to polymers which are linked by chemical bonds. The polymer can be chemically cross linked by radiation techniques such as UV-, E beam-gamma or micro-wave radiation or by co-polymerizing the monomers with a di/poly-functional crosslinker via the use e.g., of UV, thermal and/or redox polymerization initiators.

Suitable polyfunctional monomer crosslinkers include polyethyleneoxide d(meth)acrylates with varying PEG molecular weights, IRR280 (a PEG diacrylate available from UCB Chemical), trimethylolpropane ethoxylate tri (meth)acrylate with varying ethyleneoxide molecular weights, IRR210 (an alkoxylated tryacrilate: available from UCB Chemicals), trimethyolpropane tri(meth)acrylate, divinylbenzene, pentaerythritol triacrylate, pentaeythritol triallyl ether, triallyl amine, N,N-methylene-bis-acrylamide and other polyfunctional monomer crosslinkers known to the art. Preferred monomer crosslinkers include the polyfunctional diacrylates and triacrylates.

The monomers of the present invention are preferably polymerized via the use of a free radical polymerization initiator. Such free-radical polymerization initiators are well known in the art and can be one or more photoinitiator(s), thermal initiator(s), or redox initiator(s) and be present in quantities up to 5% by weight, preferably from 0.02% to 2%, more preferably from 0.02% to 0.4%. Photo initiators are preferred. Suitable photo initiators include type I-[]-hydroxy-ketones and benzyldimethyl-ketals e.g. Irgacure 651 (dimethoxybenzylphenone; available from Ciba Specialty Chemicals) which are believed, on irradiation with UV frequencies, to form benzoyl radicals that initiate polymerization. Particularly preferred photoinitiators include 2-hydroxy-2-methyl-propiophenone (available under the trade name of Darocur 1173 from Ciba Specialty Chemicals), I-hydroxycyclohexylphenylketone (available under the trade name Irgacure 184 from Ciba Specialty Chemicals) and 4-(2-hydroxyethoxy)phenyl-(2-hydroxy-2-methylpropyl) ketone (available under the trade name of Irgacure 2959 from Ciba Specialty Chemicals). Suitable thermal initiators include potassium persulfate and VA044 (available from Wako). Suitable redox initiators include the combination of hydrogen peroxide and ascorbic acid and sodium persulfate and ascorbic acid.

Chemical crosslinking can also be affected after polymerization by use of polyfunctional reagents capable of reacting with polymer functional groups such as ethyleneglycol diglycidyl ether, polyols such as glycerol, and other polyfunctional reagents known to the art.

Crosslinking can also be effected all or in part by ionic crosslinking wherein groups of opposite charge interact via ionic interactions. Suitable ionic crosslinking agents include those known to the art including polyvalent actions such as $Al^{+3}$ and $Ca^{+2}$, d/poly-amines, d/poly-quaternary ammonium compounds, including polymeric polyamines and polyquaternary ammonium compounds known to the art.

In preparing adhesive compositions in accordance with the invention, the ingredients will usually be mixed to provide a reaction mixture in the form of an initial pre-gel aqueous based liquid formulation, and this is then converted into a gel by a free radical polymerization reaction as described above. This may be achieved for example using conventional thermal initiators and/or photoinitiators or by ionizing radiation. Photoinitiation is a preferred method and will usually be applied by subjecting the pre-gel reaction mixture containing an appropriate photoinitiation agent to UV light after it has been spread or coated as a layer on siliconised release paper or other solid or porous substrate. The incident UV intensity, at a wavelength in the range from 240 to 420 nm is of sufficient intensity and exposure duration (e.g. 10–3000 mW/cm$^2$) to complete the polymerization in a reasonable time. To facilitate the process, it is often preferable to expose the reaction mixture to several UV irradiation sources, in sequence. The processing will generally be carried out in a controlled manner involving a precisely predetermined sequence of mixing and thermal treatment or history.

The total UV irradiation time should preferably be less than 300 seconds, more preferably less than 60 seconds, and even more preferably less than 10 seconds to form a gel with better than 95% conversion of the monomers, preferably more that 99.9% of monomers, even more preferably more than 99.99% of monomers. Those skilled in the art will appreciate that the extent of irradiation will be dependent on the thickness of the reaction mixture, reactivity and concentration of the monomers, concentration of photoinitiator, properties of the humectant, and nature of substrate on to which the reaction mixture is coated and the source of UV.

These timings are for high pressure mercury arc lamps as the source of UV operating at 200 W/cm. The peak intensity of UV reaching the surface of the substrate is approximately 1000 m/W/cm$^2$. For a given lamp, the UV intensity is a function of the operating power and distance of the reaction mixture from the UV source. Also, a high-pass UV filter can be employed to minimize exposure to UV intensities of very-low wavelength.

In order to minimize and preferably eliminate the presence of any residual monomers it is important to ensure that the reaction is complete. This is dependent upon a number of factors such as the substrate onto which the adhesive is applied, the type and intensity of the ultra violet light and the number of ultra violet light passes.

Optional Ingredients

Common additives known in the art such as polymerization inhibitors, chain transfer agents, surfactants, soluble or dispersible polymers, buffers, preservatives, antioxidants, pgments, mineral fillers, and the like, and mixtures thereof, may also be comprised within the adhesive composition in quantities up to 10% by weight each respoectively. Preferably, the hydrogels herein should contain no salt or minimum levels, below 1% by weight, preferably below 0.5% by weight.

pH

The pH of the hydrogel composition herein is in the range of from 3 to 6, more preferably 3 to 5.5, most preferably from 3.5 to 5.5, which represents values perfectly compatible with the pH of mammalian skin.

This pH range is directly achievable by the compositions herein, without, without the use of any additional buffering agent, which can have a detrimental impact on the performance and skin friendliness of the hydrogels herein.

The conditions of measure of the pH are described hereinafter in the test methods section.

Personal Care Products

In a second embodiment herein, the present invention is directed to Personal Care Products, capable of adhering to hair-populated skin, which contain a hydrogel adhesive having the characteristics described above, i.e. 10–60% of a cross-linked hydrophilic polymer as described above, 5–80% of a water-soluble nonionic humectant as described above, and 10–85% water, said adhesive having a $G'_{25}$ (1 rad/sec) of less than 1000 Pa, preferably 100 to 700 Pa, and which preferably has a $G''_{25}$ (1 rad/sec) in the range of 50 Pa to 1000 Pa, more preferably 100 to 700 Pa, a ratio $G''_{25}$ (1 rad/sec)/$G'_{25}$ (1 rad/sec) of from 0.15 to 0.65, preferably 0.15 to 0.55, and most preferably 0.15 to 0.55 and a peel strength force on dry skin in the range of from 0.3 to 3 N/cm.

For the purpose of the present invention, personal care products means products, disposable or reusable, which are designed to be worn by a human in contact or close proximity to the body in order to achieve a function directed to the person's heath, well-being, comfort or pleasure, and thus require temporary adhesion to the body.

A first type of such articles includes disposable, human waste management devices such as urine, menstrual and faecal management devices.

Disposable Waste-Management Devices

Urine, menstrual or faecal management devices herein include bags having an aperture and a flange surrounding the aperture for adhesive attachment to the uro genital area and or the perianal area of a wearer. Any faecal, menstrual or urine management device known in the art can be provided with an adhesive according to the present invention. Such devices are described for example in WO 99/00084 and WO 99/00085.

The urine, menstrual or faecal management devices herein also includes devices designed to be attached to artificial apertures in the body, such as ostomy/colostomy devices.

The bag as used in such articles is a flexible receptacle for the containment of urine, menstrual and excreted faecal matter.

The bag is designed to safely contain any entrapped material, typically it will be liquid impermeable, yet it may be breathable. The bag is designed of sufficient strength to withstand rupture in use, also when pressure on the bag is exerted in typical wearing conditions, such as sitting.

The bag may contain absorbent material. The absorbent material may comprise any absorbent material which is capable of absorbing and retaining liquids. The absorbent material may comprise a wide variety of liquid-absorbent materials commonly used in disposable diapers and other absorbent articles such as comminuted wood pulp, which is generally referred to as airfelt.

The human waste management device in particular urine/menstrual management devices according to the present invention may also comprise an additional acquisition layer. The acquisition layer is typically secured to the inner surface of bag. However, the acquisition layer may also be secured to the flange, or both the flange and the inner surface of bag. The acquisition layer is preferably positioned such that it separates the genitalia of the wearer from coming into direct contact with the absorbent material. The acquisition layer is fluid pervious allowing urine/menses to readily pass through so that it may be absorbed by absorbent material.

The bag is provided with an aperture whereby excreted matter is received from the body prior to storage within the bag cavity. The aperture is surrounded by a flange and may be provided in any shape or size, such as circular, oblong, heart shaped and may be symmetrical or asymmetrical, preferably the aperture has an oblong configuration either in the longitudinal or in the transversal direction or in both directions, e.g. the contours of the aperture are in the shape of two ellipses with the respective main axes being substantially perpendicular.

The flange comprises a garment facing surface and a wearer facing surface. In a preferred embodiment these are two large, substantially flat surfaces, however, the flange may also comprise projections designed to fit the perineal or coccygeal area of the wearer.

The flange should be made of soft, flexible and malleable material to allow easy placement of the flange to the perianal area. Typical materials include nonwoven materials, wovens, open celled thermoplastic foams, closed-cell thermoplastic foams, composites of open celled foams and stretch nonwoven, and films. A closed-cell foam of polyethylene has been found effective, but more preferably an open celled polyurethane foam is used. Preferably, such foams have a thickness within the general range of 0.1 to 5 millimeters and a basis weight of 5 to 250 g/m$^2$, more preferably 50 g/m$^2$. Other thermoplastic foam materials, or other suitable plastics sheet materials having the described properties of such foams (i.e., softness, pliability, stretchability, and contractibility) might also be used.

The adhesive can be applied to the wearer facing surface of the flange by any means known in the art such as slot coating, spiral, or bead application or printing. Typically the adhesive is applied at a basis weight of from 20 g/m$^2$ to 2500 g/m$^2$, more preferably from 500 g/m$^2$ to 2000 g/m$^2$ most preferably from 700 g/m$^2$ to 1500 g/m$^2$ depending on the end use envisioned. For example, for faecal management devices to be used for babies the amount of adhesive may be less than for faecal management devices designed for active adult incontinence sufferers.

Disposable Absorbent Articles

Another type of personal care articles herein include disposable absorbent articles such as diaper, sanitary napkins, pantiliners, tampons, perspiration pads. Absorbent articles are articles containing an absorbent core, and can be made by any of the ways usual in the art. The application of the adhesive to the wearer facing surface, typically the topsheet surface of an absorbent article should not cause major problems to those skilled in the art since it can be provided by any well known techniques commonly used to apply adhesives. Most preferably the adhesive is provided in a pattern of small incremental areas such as dots or similar.

This invention can be used beneficially on disposable absorbent articles which are applied directly to the skin of a user. The article usually exhibits absorbency for bodily fluids, the protection of the user's garments from soiling, is comfortable to the user, and is easy to produce and to package. The disposable absorbent article is described below by reference to a sanitary napkin or catamenial, however diapers, panty liners, adult incontinence articles, tampons or perspiration pads are also included under the term disposable absorbent articles.

Other Personal Care Products

The present invention the adhesive herein may also find application to other personal care products. The adhesives may for example find utility to adhere functional articles which adhere to the skin such as cosmetic or pharmaceutical delivery articles which provide a substance to the skin such as skin treatment substances, cream, lotions, hormones, vitamins, deodorants, drugs; cosmetic or pharmaceutical delivery articles provide a substance to emanate away from the skin such as insecticides, inhalation drugs, perfumes and; functional articles which are not necessarily attached to the skin, but which require a high residence time on the skin such as decorative cosmetics, (lipstick, eye shadow, stage make-up) and cleaning articles (hand cleaners, face masks and hygienic pore cleansers). Such articles are preferably non-absorbent for bodily liquids.

The adhesive may also in addition find application to attach articles to the skin such as protective articles such as genital-, knee- or elbow-protectors or bandages; clothing such as bras, surgical gowns, or parts of garments during fitting at a tailor; nasal plasters; prosthesis such as breast replacements or wigs; cold wraps e.g. to provide pain relief from bruises and to reduce swelling; thermal wraps comprising thermal cells as disclosed for example in WO 97/36968 and WO 97/49361 to provide relief of temporary and chronic pain such as neck wraps as disclosed in for example U.S. Pat. No. 5,728,146, knee wraps exemplified in WO 97/01311, and back wraps as disclosed for example in U.S. Pat. No. 5,741,318; hearing aids; protective face masks (for the reduction or prevention of inhalation of noxious substances); anti-snoring patches, ornamental articles such as jewellery, earrings, guises, tattoos; goggles or other eye wear, tapes, bandages, dressings of general utility, wound healing and wound management devices; and biomedical skin electrodes such as ECG, EMG, EEG, TENS electrosurgery, defibrillation, EMS and electrodes for facial/beauty applications; and fixation products and/or devices intended to affix patient catheters, tubing leadwires cables, etc.

Surface Care Articles

In a third embodiment herein, the present invention is directed to Surface Care Articles.

For the purpose of the present invention, Surface Care Articles means articles, disposable or removable, which are designed to be temporary applied to a surface in order to achieve a function directed to the treatment of said surface, and thus require temporary adhesion to said surface.

The surfaces to which the articles are particularly adapted are fiber-populated surface which includes any durable fabric used in garment upholstery, carpet as well as disposable fabrics such as nonwovens.

The treatment function to be achieved by the present invention articles can range from the permanent or temporary application of textile finishing, the cleaning of garment, upholstery or carpets, to the application on the durable or disposable fabrics, of substances such as perfumes or other actives designed to emanate from the textile.

An example of a surface-care article according to the present invention is a carpet dusting implement, containing a adhesive hydrogel according to the present invention, applied to carpets as a substitute or a complement to vacuum cleaning; the hydrogel may be present as a roll of disposable wipes rolled onto a mop, used as a carpet cleaning implement; other application of such a mop execution can be envisaged, such a dusting/cleaning of upholstery, curtains and garments.

Test Methods

1. Rheology

The rheology of hydrogels is measured at 25° C. using a RHEOMETRICS SR 5000 oscillatory rheometer or the equivalent. A sample of thickness of approximately 1 mm and diameter of 25 mm is placed between two insulated Parallel Plates of 25 mm diameter, controlled at a temperature of approximately 25° C. using a Peltier system or equivalent. A Dynamic Frequency Sweep is performed on the hydrogel in either stress or strain mode at an applied strain within the linear elastic response of the hydrogel (e.g., up to a strain of about 10%), with measurements at discrete frequency values between 0.1 and 100 rad/sec. Results are quoted as G', G" and tan delta at frequency values of 1.0 and 100 rad/sec. The hydrogel is aged at least 24 hours before measurement. The average of at least three determinations are reported.

2. Peel Force on Dry Skin

The peel force to remove hydrogel from dry skin is measured using a suitable tensile tester, for example an Instron Model 6021, equipped with a 10N load cell and an anvil rigid plate such as the Instron accessory model A50L2R-100. Samples are cut into strips of width 25.4 mm and length between about 10 and 20 cm. A non-stretchable film of length longer than the hydrogel is applied to the reverse side of the hydrogel sample (e.g., the substrate side) using double sided adhesive. A suitable film is 23μ thick PET, available from Effegidi S.p.A, 43052, Colorno, Italy. For samples with release paper, the release paper is removed prior to applying the hydrogel to the forearm and then rolling it into place using a compression weight roller to prevent air entrapment between hydrogel and skin. The roller is 13 cm in diameter, 4.5 cm wide and has a mass of 5 Kg. It is covered in rubber of 0.5 mm thickness. The free end of the backing film is attached to the upper clamp of the tensile tester and the arm is placed below. The sample is peeled from the skin at an angle of 90 degrees and a rate of 1000 mm/min. The average peel value obtained during peeling of the whole sample is quoted as the peel value in N/cm. The average of triplicate measurements is reported.

3. Peel Force on PET

Peel force to remove hydrogel from poly(ethylene teraphthalate) (PET) film is measured using a suitable tensile tester, for example an Instron Model 6021, equipped with a 10N load cell and attachment for a rigid lower plate, e.g. steel, oriented along the direction of cross-head movement. Freshly produced hydrogel is stored in a closed aluminium bag or similar for at least 12 to 24 hours at room temperature before measuring. A defect free sample of at least 10 cm in length is cut from the hydrogel sample. A piece of double sided adhesive, for example type 1524 from 3M Italia S.p.A, I-20090 Segrate, Italy, at least 130 mm long and 25.4 mm wide is stuck to the back side of the hydrogel laminate. The hydrogel is cut along the tape's outer edges. The second liner is removed from the tape and it is stuck on the rigid base plate. A strip of standard PET of 23μ thickness and no corona treatment, is cut to about 300 mm×40 mm. Suitable material would include "Cavilen-Forex" from Effegidi S.p.A, Via Provinciale per Sacca 55, I-43052 Colorno, Italy. The release liner is removed from the hydrogel and the bottom end fixed to the rigid plate by regular tape. The standard substrate is then applied onto the body adhesive using a hand roller once forward and once backward at a speed of 1000 to 5000 mm/min. The roller is 13 cm in diameter, 4.5 cm wide and has a mass of 5 Kg. It is covered in rubber of 0.5 mm thickness. The measurement is preferably performed within 10 minutes of application of the substrate.

The free end of the standard substrate is doubled back at an angle of 180 degrees and the rigid plate is clamped in the lower clamp of the tensile tester. The free end of the standard substrate is fixed in the upper clamp of the tensile tester. The peel test is performed at a speed of 1000 mm/min. The initial 20 mm of peel is disregarded and the average force over the remaining length is quoted as the peel force in N/cm. The average of triplicate measurements is reported.

4. Removal Pain Grade Test

The Removal Pain Grade Test is utilized to evaluate the pain during removal from the skin of a wearer of a sample provided with a layer of a adhesive and previously attached to the wearer's skin. The test specifically evaluates the pain upon removal of each sample as compared to the pain obtained by removing a reference sample constituted by a commercial strong medical plaster.

Sample Preparation.

The test is performed on rectangular samples 60×20 mm made of a polyester film 23 μm thick, such as that sold by Effegidi S.p.A. of Colorno (Parma, Italy), provided on one side with a continuous layer of the topical adhesive having the selected thickness, applied with an Acumeter Model LH-1 extruder. The reference sample is a 60×20 mm sample of a of an adhesive non woven fabric available from Beiersdorf A. G. Hamburg, Germany under the Tradename Fixomull stretch.

Test Method.

A panel of six graders is selected for the test. The test is performed in a climatically controlled laboratory maintained at a temperature of 23° C. and a Relative Humidity of 50%. No special treatment of the wearer's skin is required beyond normal cleaning/washing with water and soap. The skin is then allowed to dry for at least two hours before the test to allow the skin to reach equilibrium with the room conditions. Different adhesives are evaluated in the test in comparison with the reference sample R. Each sample is applied by hand by an operator to the inner part of the grader's forearm, being centred between the wrist and the elbow, with the short side of the sample aligned with the length of the arm. The operator exerts on each sample with the palm of the hand the same pressure that is typically applied to cause a medical plaster to adhere to the skin. Each sample is worn for the prescribed time, and then it is removed from the grader's skin by the operator with a slow and smooth pull.

Four series of one reference sample R and the test samples are each applied, worn and then removed from the wearer's skin; each sample is worn for one minute, with a 5 minute wait between two subsequent samples of the same series, and a 15 minute wait between two different subsequent series. The reference sample R is always applied, worn and removed as the first sample of its respective series. The sequence of application/wear/removal of the test samples in each of the first three series is random, provided that no repetition in each series is allowed, and that no sequence is repeated in the first three series. In the fourth series one of the test samples is tested twice, the reference R always being the first one. Overall each sample has to be tested an equal number of times (24 times).

The graders were asked to evaluate each sample using a pain scale ranging from 0 to 10, where 0 corresponds to no pain and 10 corresponds to the pain upon removal of the reference sample R. The pain values for each sample were obtained as a mean of 24 observations.

The results collected from the test were analysed by a statistical analysis program "Comparison of Population Means—Paired Samples", that showed that the differences between the pain values of the samples are statistically significant.

5. Fiber Embedding Test

A sample of hydrogel adhesive on a liquid-impermeable substrate with lateral dimensions greater than 35 mm is used for this test. Also used for this test is a high-loft hydrophobic non-woven with basis weight of approximately 35 gsm (for example, Sandler 4378 Sawabond non-woven or equivalent) which has lateral dimensions equal to or greater than that of the hydrogel. Prior to use, the back side of this non-woven (the non-high-loft side) is covered with (i) a double sided adhesive (for example type 1524 from 3M Italia S.p.A, I-20090 Segrate, Italy) and (ii) a piece of standard PET of 23μ thickness and no corona treatment, (for example "Cavilen-Forex" from Effegidi S.p.A, Via Provinciale per Sacca 55, I-43052 Colorno, Italy). The hydrogel sample is applied co-facially on top of the nonwoven with the adhesive side of the hydrogel in contact with the high-loft side. An approximately 35 mm diameter circular piece of the hydrogel/non-woven sandwich structure is cut from the larger piece using a circular punch or equivalent of inner diameter of approximately 35 mm and weighed to an accuracy of at least 0.001 g ($W_{35}$). A compression weight roller with a diameter of approximately 13 cm and a mass of approximately 5 Kg, which is covered in rubber of approximately 0.5 mm thickness, is used to compress the resultant 35 mm diameter piece of hydrogel/non-woven sandwich structure by rolling the compression weight on top of the piece first forward and then backward. The compressed circular piece of hydrogel/non-woven sandwich is positioned with the non-woven side down in a dry container and covered with a cylindrical stainless steel weight of diameter approximately 50 mm and weight of approximately 240 gm. To this container is then added a sufficient volume of 0.9% saline solution, containing approximately 0.01 wt % of Indigo Carmine Blue Dye, to completely cover the sandwich structure. After an immersion time of approximately 60 minutes, the test sample is removed from the saline and the outer surfaces are blotted dry. An approximately 25 mm diameter piece is cut from the center of the 35 mm diameter test sample using a circular punch or equivalent having an inner diameter of approximately 25 mm and weighed to an accuracy of at least 0.001 g ($W_{25}$). By cutting away the outer 5 mm wide ring of the test sample, hydrogel that is swollen solely by diffusive contact with the saline is removed. This central 25 mm diameter piece is also visually checked for the appearance of blue color. The weight gain of the central 25 mm diameter inner section of the hydrogel in percent as a result of immersion of the larger 35 mm test piece in saline is calculated using the following equation:

$$\text{Weight Gain } (\%)=100*\{(W_f-W_i)/W_i\}/F$$

where, $$F=\{W_{35}-(BW_{nws}*A_{35})-(BW_{substrate}*A_{35})\}/W_{35}$$

and $W_i=W_{35}*A_{25}/A_{35}$ $W_f=W_{25}$ $W_{35}$=Dry weight of 35 mm circular piece of hydrogel/non-woven in grams $A_{35}$=Area of 35 mm circular piece of hydrogel/non-woven in cm$^2$ $A_{25}$=Area of 25 mm circular piece of hydrogel/non-woven in cm$^2$ $W_{25}$=Weight of 25 mm inner circle of hydrogel/non-woven after Immersion in grams $BW_{nws}$=Weight per unit area of non-woven structure in units of g/cm$^2$ $BW_{substrate}$=Weight per unit area of hydrogel substrate in units of g/cm$^2$ The average of at least triplicate determinations are used to calculate the Percentage Weight Gain.

For good fiber embedding into the hydrogel, there are relatively few capillary paths for the saline solution to wick between the hydrogel and the hydrophobic backing of the non-woven and thus there is a low percentage weight gain (e.g., <5%) for the hydrogel in the 25 mm inner circle of hydrogel. There is also a minimal appearance of blue color in this central section of hydrogel. For poor fiber embedding, there are many capillary pathways and thus there is a greater weight gain (e.g., >5%). There is also a significant appearance of blue color in this central section of hydrogel.

EXAMPLES

Hydrogel adhesive compositions having the compositions described in examples 1, 2 and 3 below are used for adhesion on hairy skin Example 1

An aqueous solution of sodium hydroxide is prepared by dissolving approximately 8.0 parts sodium hydroxide (Aldrich; ACS reagent grade) in approximately 33.8 parts of distilled water. After cooling to ambient temperature, approximately 20.7 parts of acrylic acid (Aldrich, 99%) is added. The resultant solution contains a mixture of acrylic acid and sodium acrylate in a molar ratio of approximately 3:7. After cooling to ambient temperature, approximately 37.4 parts of glycerol (Agrar) is added to this solution. The resultant mixture is stirred for approximately 15 minutes. Separately, a solution is prepared by dissolving approximately 6.0 parts of the photoinitiator Irgacure 184 (1-hydroxy-cyclohexyl-phenyl-ketone; CIBA Specialty Chemicals) in approximately 20 parts of the crosslinker IRR-210 (alkoxylated triacrylate, Mw~800; UCB Chemicals). Approximately 0.14 parts of the resultant crosslinker/photoinitiator solution is added to approximately 99.9 parts of the glycerol/water solution of partially-neutralized acrylic acid, followed by stirring for approximately 20 minutes.

One fraction of the monomer solution is spread at a basis weight of approximately 1.0 kilograms per square meter onto a siliconized release paper (Silk Kraft 70GR; Cogesil SpA), that has been surface treated by wiping with a very-thin layer of Pluronic 6400 surfactant (BASF) to facilitate spreading of the solution. For handling purposes, the release paper is pre-positioned inside a 8.5 cm diameter polystyrene Petri dish. A second fraction of the monomer solution is coated at a basis weight of approximately 1.0 kilogram per square meter onto a thin, porous non-woven substrate (Fiberweb 33; Corolind PE; 33 g/sqm). This non-woven is backed by a PET film (Cavilen-Forex; 23 $\mu$m), which is attached to the non-woven by 3M 1524 double-sided adhesive. This non-woven is pre-positioned inside a shallow rectangular 20 cm by 12 cm Plexiglass box. The solution is added dropwise over the surface of the non-woven and then spread by gently tilting the box from side-to-side. An IST Model # M20-1 (2)-TR-SLC UV Polymer Reactor, equipped with an IST 200 ozone-free arc lamp (Spectrum Type: CKII-OF) is used to effect polymerization. The monomer-coated substrate is irradiated while passing underneath the lamp on a variable-speed belt positioned approximately 10 cm underneath the lamp. The speed of the belt is set at approximately seven meter/min. The peak output power of the lamp is measured using an UMS-1 power meter (Eta Plus Electronic) and the output intensity of the lamp is adjusted so that the incident peak UV power on the sample is approximately 1200 milliwatt/cm$^2$. Twelve consecutive passes of the sample underneath the lamp is used to polymerize the monomer solution and convert it into a soft adhesive hydrogel useful for embedding of hair.

The resultant hydrogels are analyzed as follows. From the sample polymerized on release paper, a 25 mm diameter punch is used to obtain a circular sample of hydrogel for measurement of rheology properties. The punched section is transferred to the upper plate of a Rheometrics RDA II oscillatory rheometer. The release paper is removed from the hydrogel and the hydrogel is contacted with the lower plate of the rheometer. The dependence of G' and G" on frequency (1.0–100 rad/sec) is measured at 25° C. using standard procedures. The thickness of the sample is obtained from the plate-to-plate separation used for the rheology measurement. A 16 cm by 1 inch strip is cut from the hydrogel sample formed on the non-woven substrate. This strip is used to measure the peel force of the adhesive using procedures described.

Test results for the hydrogel of Example 1 are summarized in Table 1. Evaluation of the hydrogel sample by expert graders indicate that the hydrogel of this example, is effective at embedding hair.

Example 2

The procedure described in Example 1 is followed except for the following changes. The aqueous sodium hydroxide solution is prepared by dissolving approximately 7.7 parts sodium hydroxide in approximately 34.6 parts of distilled water. Approximately 19.8 parts of acrylic acid is added. Approximately 38 parts of glycerol is added to this solution.

Test results for the hydrogel of Example 2 are summarized in Table 1. Evaluation of the hydrogel sample by expert graders indicate that the hydrogel of this example is effective at embedding hair.

Example 3

An aqueous solution of potassium 3-sulphopropyl acrylate (KSPA; Aldrich) is prepared by dissolving approximately 34.3 parts KSPA in approximately 34.3 parts of distilled water. This solution is mixed with approximately 31.3 parts of glycerol (Agrar) and stirred for approximately 10 minutes. Separately, a solution is prepared by dissolving approximately 6.0 parts of the photoinitiator Irgacure 184 (1-hydroxy-cyclohexyl-phenyl-ketone; CIBA Specialty Chemicals) in approximately 20 parts of the crosslinker IRR-210 (alkoxylated triacrylate, Mw~800; UCB Chemicals). Approximately 0.14 parts of the resultant crosslinker/photoinitiator solution is added to the KSPA solution, followed by stirring for approximately 20 minutes. The procedure described in Example 1 is then followed.

Test results for the hydrogel of Example 3 are summarized in Table 1. Evaluation of the hydrogel sample by expert graders indicate that the hydrogel of this example is effective at embedding hair.

TABLE 1

Test Results for Adhesive Hydrogels of Examples 1–3

| Hydrogel (Ex #) | G' (25° C.) (Pa; 1 rad/s) | G" (25° C.) (Pa; 1 rad/s) | Tan □ (1 rad/s) | Peel Force on dry skin (N/cm) | Hair Embedding Visual Inspection |
|---|---|---|---|---|---|
| 1 | 840 | 630 | 0.75 | 1.7 | Good |
| 2 | 570 | 470 | 0.82 | 1.9 | Good |
| 3 | 270 | 180 | 0.67 | 0.94 | Good |

What is claimed:

1. A personal care product comprising:
   (a) an article selected from the group consisting of disposable waste management articles, absorbent articles, functional articles, and combinations thereof;
   (b) wherein said article, comprises a hydrogel adhesive, said adhesive comprising from 10 weight percent to 60 weight percent of a cross-linked hydrophilic polymer; from 5 weight percent to 80 weight percent of a water soluble nonionic humectant, and from 10 weight percent to 85 weight percent of water, said adhesive having an elastic modulus at a temperature of 25° C., $G'_{25}$(1 rad/sec), less than 500 Pa and wherein the hydrogel adhesive has substantially no adhesion to hair on a skin surface.

2. The personal care product of claim 1, wherein said $G'_{25}$(1 rad/sec) ranges from 100 Pa to 500 Pa.

3. The personal care product of claim 1, wherein said adhesive has a viscous modulus at a temperature of 25° C., $G''_{25}$(1 rad/sec), ranging from 50 Pa to 1000 Pa, a ratio $G''_{25}$(1 rad/sec)/$G'_{25}$(1 rad/sec) ranging from 0.15 to 0.65, and a peel strength force on dry skin ranging from 0.3 N/cm to 2 N/cm.

4. The personal care product of claim 1, wherein said article is a disposable human waste management article comprising a bag, said bag comprising an aperture and a flange surrounding said aperture, said flange comprising a wearer-facing surface, wherein said hydrogel adhesive is disposed on said wearer-facing surface.

5. The personal care product of claim 1, wherein said article is an absorbent article comprising an absorbent core and a wearer-facing surface, said hydrogel adhesive being disposed on said wearer-facing surface.

6. The personal care product of claim 1, wherein said functional article is selected from the group consisting of cosmetic delivery articles, pharmaceutical delivery articles, decorative cosmetic articles, cleaning articles, protective articles, clothing, prosthesis, cold wraps, thermal wraps, hearing aids, ornamental articles, goggles and eye wear, said functional article comprising a wearer-facing surface, said hydrogel adhesive being disposed on said wearer-facing surface.

7. A surface care article comprising a hydrogel adhesive capable of adhesion on fiber populated surfaces, said hydrogel adhesive comprising from 10 weight percent to 60 weight percent of a cross-linked hydrophilic polymer, from 5 weight percent to 80 weight percent of a water-soluble nonionic humectant, and from 10 weight percent to 85 weight percent of water, said adhesive having an elastic modulus at a temperature of 25° C. $G'_{25}$(1 rad/sec) less than 500 Pa and wherein the hydrogel adhesive has substantially no adhesion to hair on a skin surface.

8. The surface care article of claim 7, wherein $G'_{25}$(1 rad/sec) ranges from 100 Pa to 500 Pa.

* * * * *

UNITED STATES PATENT AND TRADEMARK OFFICE
CERTIFICATE OF CORRECTION

PATENT NO.    : 6,921,574 B2
DATED         : July 26, 2005
INVENTOR(S)   : Cinelli et al.

It is certified that error appears in the above-identified patent and that said Letters Patent is hereby corrected as shown below:

Column 6,
Line 8, delete "E beam-gamma" and insert -- E beam-. gamma --.

Column 8,
Line 4, delete "rad/sec)/G"$_{25}$" and insert -- rad/sec)G'$_{25}$ --.

Signed and Sealed this

Eighteenth Day of October, 2005

JON W. DUDAS
*Director of the United States Patent and Trademark Office*